(12) United States Patent
Villongco et al.

(10) Patent No.: US 11,534,224 B1
(45) Date of Patent: Dec. 27, 2022

(54) INTERACTIVE ABLATION WORKFLOW SYSTEM

(71) Applicant: Vektor Medical, Inc., Carlsbad, CA (US)

(72) Inventors: Christopher J. T. Villongco, Roswell, GA (US); Robert Joseph Krummen, Bellevue, WA (US)

(73) Assignee: Vektor Medical, Inc., Carlsbad, CA (US)

(*) Notice: Subject to any disclaimer, the term of this patent is extended or adjusted under 35 U.S.C. 154(b) by 0 days.

(21) Appl. No.: 17/541,040

(22) Filed: Dec. 2, 2021

(51) Int. Cl.
*G16H 20/30* (2018.01)
*A61B 18/00* (2006.01)
(Continued)

(52) U.S. Cl.
CPC .............. *A61B 18/00* (2013.01); *G06N 20/00* (2019.01); *G16H 20/30* (2018.01); *G16H 50/20* (2018.01); *G16H 50/30* (2018.01); *A61B 2018/00351* (2013.01); *A61B 2018/00577* (2013.01); *A61B 2018/00839* (2013.01)

(58) Field of Classification Search
CPC .......... G16H 20/40; A61B 2018/00351; A61B 2018/00577; A61B 2018/00839
See application file for complete search history.

(56) References Cited

U.S. PATENT DOCUMENTS 4,352,163 A 9/1982 Schultz et al.
5,458,116 A 10/1995 Egler
(Continued)

FOREIGN PATENT DOCUMENTS

CN 105263405 A 1/2016
CN 106725428 5/2017
(Continued)

OTHER PUBLICATIONS

Andreu et al., "Integration of 3D Electroanatomic Maps and Magnetic Resonance Scar Characterization into the Navigation System to Guide Ventricular Tachycardia Ablation", Circ Arrhythm Electrophysiol, Oct. 2011, 4(5), pp. 674-683.
(Continued)

*Primary Examiner* — John R Downey
(74) *Attorney, Agent, or Firm* — Perkins Coie LLP

(57) ABSTRACT

A method is provided for treating a patient with an arrhythmia. In some embodiments, the method collects a first patient arrhythmia cardiogram from the patient. The method identifies a first target location and a first ablation pattern associated with a first library arrhythmia cardiogram that is similar to the first patient arrhythmia cardiogram. The method then performs a first ablation near the first target location, factoring in the first ablation pattern, and after the ablation, collects a second patient arrhythmia cardiogram of the patient. The method continues to identify a second target location and a second ablation pattern associated with a second library arrhythmia cardiogram that is similar to the second patient arrhythmia cardiogram. The second library arrhythmia cardiogram is identified, in part, based on ablation characteristics of the first ablation. The method then performs a second ablation near the second target location, factoring in the second ablation pattern.

20 Claims, 5 Drawing Sheets

(51) Int. Cl.
*G16H 50/30* (2018.01)
*G06N 20/00* (2019.01)
*G16H 50/20* (2018.01)

(56) References Cited

U.S. PATENT DOCUMENTS

| | | | |
|---|---|---|---|
| 5,596,634 | A | 1/1997 | Fernandez et al. |
| 5,601,084 | A | 2/1997 | Sheehan |
| 5,803,084 | A | 9/1998 | Olson |
| 5,891,132 | A | 4/1999 | Hohla |
| 6,269,336 | B1 | 7/2001 | Ladd et al. |
| 6,292,783 | B1 | 9/2001 | Rohler et al. |
| 6,324,513 | B1 | 11/2001 | Nagai et al. |
| 6,370,412 | B1 | 4/2002 | Armoundas et al. |
| 6,567,805 | B1 | 5/2003 | Johnson et al. |
| 6,895,084 | B1 | 5/2005 | Saylor et al. |
| 6,931,273 | B2 | 8/2005 | Groenewegen et al. |
| 7,010,347 | B2 | 3/2006 | Schecter |
| 7,286,866 | B2 | 10/2007 | Okerlund et al. |
| 8,224,640 | B2 | 7/2012 | Sharma et al. |
| 8,521,266 | B2 | 8/2013 | Narayan |
| 8,838,203 | B2 | 9/2014 | Van Dam et al. |
| 8,849,389 | B2 | 9/2014 | Anderson et al. |
| 9,014,795 | B1 | 4/2015 | Yang |
| 9,129,053 | B2 | 9/2015 | Mansi et al. |
| 9,277,970 | B2 | 3/2016 | Mansi et al. |
| 9,320,126 | B2 | 4/2016 | Valcore, Jr. |
| 9,706,935 | B2 | 7/2017 | Spector |
| 9,842,725 | B2 | 12/2017 | Valcore, Jr. |
| 10,039,454 | B2 | 8/2018 | Sapp, Jr. et al. |
| 10,311,978 | B2 | 6/2019 | Mansi et al. |
| 10,319,144 | B2 | 6/2019 | Krummen et al. |
| 10,342,620 | B2 | 7/2019 | Kiraly et al. |
| 10,363,100 | B2 | 7/2019 | Trayanova et al. |
| 10,556,113 | B2 | 2/2020 | Villongco |
| 10,617,314 | B1 | 4/2020 | Vektor |
| 10,713,790 | B2 | 7/2020 | Adler |
| 10,860,754 | B2 | 12/2020 | Villongco |
| 10,861,246 | B2 | 12/2020 | Voth |
| 11,259,871 | B2 | 3/2022 | Villongco et al. |
| 2001/0049688 | A1 | 12/2001 | Fratkina et al. |
| 2002/0010679 | A1 | 1/2002 | Felsher |
| 2002/0154153 | A1 | 10/2002 | Messinger |
| 2002/0188599 | A1 | 12/2002 | McGreevy |
| 2003/0182124 | A1 | 9/2003 | Khan |
| 2004/0059237 | A1* | 3/2004 | Narayan .......... A61B 5/35 607/9 |
| 2004/0083092 | A1 | 4/2004 | Valles |
| 2004/0176697 | A1 | 9/2004 | Kappenberger |
| 2007/0031019 | A1 | 2/2007 | Lesage |
| 2007/0032733 | A1 | 2/2007 | Burton |
| 2007/0060829 | A1* | 3/2007 | Pappone ............ A61B 18/1492 600/509 |
| 2007/0219452 | A1 | 9/2007 | Cohen et al. |
| 2008/0077032 | A1 | 3/2008 | Holmes et al. |
| 2008/0140143 | A1 | 6/2008 | Ettori |
| 2008/0177192 | A1 | 7/2008 | Chen |
| 2008/0205722 | A1 | 8/2008 | Schaefer |
| 2008/0234576 | A1 | 9/2008 | Gavit-Houdant et al. |
| 2008/0288493 | A1 | 11/2008 | Yang et al. |
| 2009/0099468 | A1* | 4/2009 | Thiagalingam ........ A61B 5/349 600/515 |
| 2009/0275850 | A1 | 11/2009 | Mehendale |
| 2010/0266170 | A1 | 10/2010 | Khamene |
| 2011/0028848 | A1 | 2/2011 | Shaquer |
| 2011/0118590 | A1 | 5/2011 | Zhang |
| 2011/0251505 | A1 | 10/2011 | Narayan |
| 2011/0307231 | A1 | 12/2011 | Kirchner |
| 2012/0173576 | A1 | 7/2012 | Gillam et al. |
| 2013/0006131 | A1 | 1/2013 | Narayan |
| 2013/0096394 | A1 | 4/2013 | Gupta |
| 2013/0131529 | A1 | 5/2013 | Jia |
| 2013/0131629 | A1 | 5/2013 | Jia |
| 2013/0150742 | A1 | 6/2013 | Briggs |
| 2013/0197881 | A1 | 8/2013 | Mansi et al. |
| 2013/0268284 | A1 | 10/2013 | Heck |
| 2013/0304445 | A1 | 11/2013 | Iwamura et al. |
| 2014/0005562 | A1 | 1/2014 | Bunch |
| 2014/0088943 | A1 | 3/2014 | Trayanova et al. |
| 2014/0107511 | A1 | 4/2014 | Banet |
| 2014/0122048 | A1 | 5/2014 | Vadakkumpadan et al. |
| 2014/0200575 | A1 | 7/2014 | Spector |
| 2014/0276152 | A1 | 9/2014 | Narayan |
| 2015/0005652 | A1 | 1/2015 | Banet et al. |
| 2015/0057522 | A1 | 2/2015 | Nguyen |
| 2015/0216432 | A1 | 8/2015 | Yang |
| 2015/0216434 | A1 | 8/2015 | Ghosh |
| 2015/0216438 | A1 | 8/2015 | Bokan et al. |
| 2015/0294082 | A1 | 10/2015 | Passerini et al. |
| 2016/0008635 | A1 | 1/2016 | Burdette |
| 2016/0038743 | A1 | 2/2016 | Foster et al. |
| 2016/0113725 | A1 | 4/2016 | Trayanova et al. |
| 2016/0135702 | A1 | 5/2016 | Perez |
| 2016/0135706 | A1 | 5/2016 | Sullivan |
| 2016/0192868 | A1 | 7/2016 | Levant et al. |
| 2016/0331337 | A1 | 11/2016 | Ben-Haim |
| 2017/0027649 | A1 | 2/2017 | Kiraly |
| 2017/0061617 | A1 | 3/2017 | Cochet |
| 2017/0065195 | A1 | 3/2017 | Nguyen |
| 2017/0068796 | A1 | 3/2017 | Passerini et al. |
| 2017/0079542 | A1 | 3/2017 | Spector |
| 2017/0150928 | A1 | 6/2017 | del Alamo de Pedro |
| 2017/0156612 | A1 | 6/2017 | Relan |
| 2017/0161439 | A1 | 6/2017 | Raduchel et al. |
| 2017/0161896 | A1 | 6/2017 | Blake, III |
| 2017/0178403 | A1 | 6/2017 | Krummen |
| 2017/0185740 | A1 | 6/2017 | Seegerer |
| 2017/0202421 | A1 | 7/2017 | Hwang et al. |
| 2017/0202521 | A1 | 7/2017 | Urman et al. |
| 2017/0209698 | A1 | 7/2017 | Villongco |
| 2017/0231505 | A1 | 8/2017 | Mahajan |
| 2017/0273588 | A1 | 9/2017 | He |
| 2017/0027465 | A1 | 11/2017 | Blauer |
| 2017/0319089 | A1 | 11/2017 | Lou |
| 2017/0319278 | A1 | 11/2017 | Trayanova |
| 2017/0330075 | A1 | 11/2017 | Tuysuzoglu |
| 2017/0367603 | A1 | 12/2017 | Spector |
| 2018/0012363 | A1 | 1/2018 | Seiler |
| 2018/0020916 | A1 | 1/2018 | Ruppersberg |
| 2018/0260706 | A1 | 9/2018 | Galloway et al. |
| 2018/0279896 | A1 | 10/2018 | Ruppersberg |
| 2018/0318606 | A1 | 11/2018 | Robinson |
| 2019/0038363 | A1* | 2/2019 | Adler ................. A61B 34/25 |
| 2019/0060006 | A1 | 2/2019 | Van Dam |
| 2019/0069795 | A1 | 3/2019 | Kiranya |
| 2019/0104951 | A1 | 4/2019 | Valys |
| 2019/0104958 | A1 | 4/2019 | Rappel |
| 2019/0125186 | A1 | 5/2019 | Ruppersberg |
| 2019/0216350 | A1 | 7/2019 | Sullivan et al. |
| 2019/0223946 | A1 | 7/2019 | Coates |
| 2019/0304183 | A1 | 10/2019 | Krummen |
| 2019/0328254 | A1 | 10/2019 | Villongco |
| 2019/0328257 | A1 | 10/2019 | Villongco |
| 2019/0328457 | A1* | 10/2019 | Villongco .......... A61B 18/1206 |
| 2019/0328458 | A1 | 10/2019 | Shmayahu |
| 2019/0332729 | A1* | 10/2019 | Villongco ............. G16H 30/40 |
| 2019/0333639 | A1 | 10/2019 | Villongco |
| 2019/0333641 | A1 | 10/2019 | Villongco |
| 2019/0333643 | A1* | 10/2019 | Villongco ............. G06T 17/20 |
| 2020/0324118 | A1 | 10/2020 | Garner et al. |
| 2021/0015390 | A1 | 1/2021 | Zhou et al. |
| 2021/0205025 | A1 | 7/2021 | Erkamp et al. |

FOREIGN PATENT DOCUMENTS

| | | |
|---|---|---|
| CN | 113851225 A | 12/2021 |
| JP | H08289877 A | 11/1996 |
| JP | 2017-140381 A | 8/2017 |
| WO | 2015153832 A1 | 10/2015 |
| WO | 2018190715 A1 | 10/2018 |
| WO | 2019118640 A1 | 6/2019 |
| WO | WO-2020101864 A1 * 5/2020 ......... A61B 18/1492 |
| WO | WO-2020142539 A1 * 7/2020 |

(56) References Cited

FOREIGN PATENT DOCUMENTS

OTHER PUBLICATIONS

Acharya et al., A deep convolutional neural network model to classify heartbeats, Computers in Biology and Medicine (Oct. 1, 2017) vol. 89, pp. 389-396.

Acharya et al., Deep convolutional neural network for the automated detection and diagnosis of seizure using EEG signals, Computers in Biology and Medicine (Sep. 1, 2018, Epub Sep. 27, 2017) 100:270-278.

Carrault, Guy, et al. "A model-based approach for learning to identify cardia arrhythias," Joint European Conference on Artificial Intelligence in Medicine and Medicine Decision Making. Springer, Berline Heidelberg, 1999.

Carrualt, Guy, et al. "Temporal abstraction and inductive logic programming for arrhythima recognition from electrocardiograms." Artificial intelligence in medicine 28.3 (2003): 231-263.

Cobb, Leonard A., et al. "Changing incidence of out-of-hospital ventricular fibrillation, 1980-2000." Jama 288.23 (2002): 3008-3013.

Cuculich, Phillip S et al., "Noninvasive Cardiac Radiation for Ablation of Ventricular Tachycardia" New England Journal of Medicine, 377; 24, pp. 2325-2336, Dec. 14, 2017.

Dandu Ravi Varma, "Managing DICOM images: Tips and tricks for the radiologist", Indian J Radiol Imaging., Jan.-Mar. 2012;22(1), pp. 4-13.

Extended European Search Report issued in European Patent Application No. 19215701.4 and dated Apr. 17, 2020, 9 pages.

Extended European Search Report issued in European Patent Application No. 19792821.1 and dated Mar. 15, 2021. 10 pages.

Frank, Ernest, "An Accurate, Clinically Practical System for Spatial Vectorcardiography," American Heart Association, Inc., downloaded from http://circ.ahajournals.org/ at Cons California Dig Lib on Mar. 12, 2014.

Gonzales, Matthew J., et al. "Structural contributions to fibrillatory rotors in a patient-derived computational model of the atria." EP Europace 16.suppl 4 (2014): iv3-iv10.

Graham, Adam J. et al., "Evaluation of ECG Imaging to Map Haemodynamically Stable and Unstable Ventricular Arrhythmias" downloaded from http://ahajournals.org on Jan. 22, 2020.

Hren, Rok, et al. "Value of simulated body surface potential maps as templates in localizing sites of ectopic activation for radiofrequency ablation" Physiol. Meas. 18 (1997) 373-400. Mar. 7, 1997.

International Search Report and Written Opinion issued for PCT/US16/68449 dated Mar. 29, 2017.

International Search Report and Written Opinion issued for PCT/US2019/029181 dated Sep. 16, 2019.

International Search Report and Written Opinion issued for PCT/US2019/029184 dated Sep. 24, 2019.

International Search Report and Written Opinion issued for PCT/US2019/058217 dated Feb. 7, 2020, 9 pages.

International Search Report and Written Opinion issued for PCT/US2019/069136 dated May 11, 2020, 13 pages.

International Search Report and Written Opinion issued in PCT/US2020/036754 dated Oct. 15, 2020, 13 pages.

Jacquemet, V., "Lessons from Computer Simulation of Ablation of Atrial Fibrillation", J Physiol. 594(9): 2417-2430, May 1, 2016.

Kiranyaz et al., Real-time patient-specific EDG classification by 1-D convolutional neural networks, IEEE Transactions on Biomedical Engineering (Mar. 2016) 63:664-675.

Kors, J.A., et al., "Reconstruction of the Frank vectorcardiogram from standard electrocardiographic leads: diagnostic comparison of different methods," European Heart Journal, vol. 11, Issue 12, Dec. 1, 1990, pp. 1083-1092.

Krishnamurthy, Adarsh, et al. "CRT Response is Greater in Patients with Larger Fraction of the Myocardium Performing Negative Regional Work." Circulation 128.Suppl 22 (2013): A11135-A11135, Abstract only.

Krishnamurthy, Adarsh, et al. "Patient-specific models of cardiac biomechanics." Journal of computational physics 244 (2013): 4-21.

Krummen, David E., et al. "Rotor stability separates sustained ventricular fibrillation from self-terminating episodes in humans." Journal of the American College of Cardiology 63.24 (2014) 2712-2721.

Lyon, et al. J.R. Soc Interface vol. 15:1-18. (2017).

Nash, Martyn P., et al. "Evidence for multiple mechanisms in human ventricular fibrillation." Circulation 114.6 (2006): 536-542.

Potse, Mark et al., "Continuous Localization of Cardian Activation Sites Using a Database of Multichannel ECG Recordings" IEEE Transactions of Biomedical Engineering, vol. 47, No. 5, May 2000, pp. 682-689.

Rahhal et al., Convolutional neural networks for electrocardiogram classification, Journal of Medical and Biological Engineering (Mar. 30, 2018) 38:1014-1025.

Sapp, John L. et al., "Real-Time Localization of Ventricular Tachycardia Origin From the 12-Lead Electrocardiogram" JACC: Clinical Electrophysiology by the American College of Cardiology Foundation, vol. 3, No. 7, Jul. 2017, pp. 687-699.

Si, Hang, "TetGen, a Delaunay-Based Quality Tetrahedral Mesh Generator," ACM Transactions on Mathematical Software, vol. 41, No. 2, Article 11, Jan. 2015, 36 pages.

Siregar, P. "An Interactive Qualitative Model in Cardiology" Computers and Biomedical Research 28, pp. 443-478, May 16, 1994.

Taggart, Peter, et al. "Developing a novel comprehensive framework for the investigation of cellular and whole heart electrophysiology in the in situ human heart: Historical perspectives, current progress and future prospects." Progress in biophysics and molecular biology 115.2-3 (2014): 252-260.

Tajbakhsh, Nima et al., "Convolutional Neural Networks for Medical Image Analysis: Full Training or Fine Tuning?" IEEE Transactions on Medical Imaging (2016) vol. 35, e-pp. 1-17).

Ten Tusscher et al. "A model for human ventricular tissue." American Journal of Physiology-Heart and Circulatory Physiology 286.4 (2004): H1573-H1589.

Thakor and Tong (Annual Reviews in Biomedicine and Engineering (2004) vol. 6, 453-495).

Tobon, Catalina, et al. "Dominant frequency and organization index maps in a realistic three-dimensional computational model of atrial fibrillation." Europace; 14, suppl_5 (2012): v25-v32.

Tomašić, Ivan et al., "Electrocardiographic Systems with Reduced Numbers of Leads—Synthesis of the 12-Lead ECG," IEEE Reviews in Biomedical Engineering, vol. 7, 2014, pp. 126-142.

Vadakkumpadan, Fijoy, et al. "Image-based estimation of ventricular fiber orientations for personalized modeling of cardiac electrophysiology." IEEE-TMI 31.5 (2012): 1051-1060.

Villongco, Christopher T., et al. "Patient-specific modeling of ventricular activation pattern using surface ECG-derived vectorcardiogram in bundle branch block." Progress in biophysics and molecular biology 115.2 (2014): 305-313.

Vozda, M et al., "Methods for derivation of orthogonal leads from 12-lead electrocardiogram: A review," Elsevier, Biomedical Signal Processing and Control 19 (2015), 23-34.

Xiong et al. Computing in Cardiology vol. 44: pp. 1-4. (2017).

Zhou, Shijie et al. "Localization of ventricular activation origin using patient-specific geometry: Preliminary results" J. Carciovasc Electrophysiology, 2018; 29: pp. 979-986.

Zhou, Shijie et al. "Rapid 12-lead automated localization method: Comparison to electrocardiographic imaging (ECGI) in patient-specific geometry", Journal of Electrocardiology, vol. 51, 2018, pp. S92-S97.

Light, D., E., et al. "Two Dimensional Arrays for Real Time Volumetric and Intracardiac Imaging with Simultaneous Electrocardiogram", 1196-2000 IEEE Ultrasonics Symposium, retrieved on Sep. 24, 2021.

Zhang, C., et al. "Patient-Specific ECG Classification Based on Recurrent Neural Networks and Clustering Technique," Proceedings of the IASTED International Conference in Biomedical Engineering (Bio Med 2017); Feb. 20-21, 2017 in Innsbruck, Austria, 5 pages.

(56) References Cited

OTHER PUBLICATIONS

International Searching Authority, International Search Report and Written Opinion, PCT Patent Application PCT/US2021/057616, dated Jan. 28, 2022, 9 pages.
He, Zhenliang et al., Facial Attribute Editing by Only Changing What You Want, IEEE Transactions on Image Processing, 2018.
Goodfellow, Ian et al., Generative Adversarial Nets, Advances in Neural Information Processing Systems, pp. 2672-2680, 2014.

* cited by examiner

INTERACTIVE ABLATION WORKFLOW SYSTEM

BACKGROUND

Many heart disorders can cause symptoms, morbidity (e.g., syncope or stroke), and mortality. Common heart disorders caused by arrhythmias include inappropriate sinus tachycardia (IST), ectopic atrial rhythm, junctional rhythm, ventricular escape rhythm, atrial fibrillation (AF), ventricular fibrillation (VF), focal atrial tachycardia (focal AT), atrial microreentry, ventricular tachycardia (VT), atrial flutter (AFL), premature ventricular complexes (PVCs), premature atrial complexes (PACs), atrioventricular nodal reentrant tachycardia (AVNRT), atrioventricular reentrant tachycardia (AVRT), permanent junctional reciprocating tachycardia (PJRT), and junctional tachycardia (JT). The sources of arrhythmias may include electrical rotors (e.g., ventricular fibrillation), recurring electrical focal sources (e.g., atrial tachycardia), anatomically based reentry (e.g., ventricular tachycardia), and so on. These sources are important drivers of sustained or clinically significant arrhythmia episodes. Arrhythmias can be treated with ablation using different technologies, including radiofrequency energy ablation, cryoablation, ultrasound ablation, laser ablation, external radiation sources, directed gene therapy, and so on by targeting the source of the heart disorder. Since the sources of heart disorders and the locations of the source vary from patient to patient, even for common heart disorders, targeted therapies require the source of the arrhythmia to be identified.

Unfortunately, current methods for reliably identifying the source locations of the source of a heart disorder can be complex, cumbersome, and expensive. For example, one method uses an electrophysiology catheter having a multi-electrode basket catheter that is inserted into the heart (e.g., left ventricle) intravascularly to collect from within the heart measurements of the electrical activity of the heart, such as during an induced episode of VF. The measurements can then be analyzed to help identify a possible source location. Presently, such basket catheters are expensive (and generally limited to a single use) and may lead to serious complications, including cardiac perforation and tamponade. Another method uses an exterior body surface vest with electrodes to collect measurements from the patient's body surface, which can be analyzed to help identify an arrhythmia source location. Such body surface vests are expensive, are complex and difficult to manufacture, and may interfere with the placement of defibrillator pads needed after inducing VF to collect measurements during the arrhythmia. In addition, the vest analysis requires a computed tomography (CT) scan, and resolution is suboptimal for the interventricular and interatrial septa where approximately 20% of arrhythmia sources may occur.

A further difficulty with common techniques for performing an ablation occurs when an ablation is determined to be unsuccessful—that is, the patient continues to experience an arrhythmia after the ablation. Such an unsuccessful ablation may not be identified until after the patient leaves the medical facility and the arrhythmia then occurs, sometimes leading to death. When an ablation is determined to be unsuccessful either before or after the patient leaves the medical facility, a process similar to that described above would need to be repeated with the associated costs and risks.

DETAILED DESCRIPTION

Figure 1:
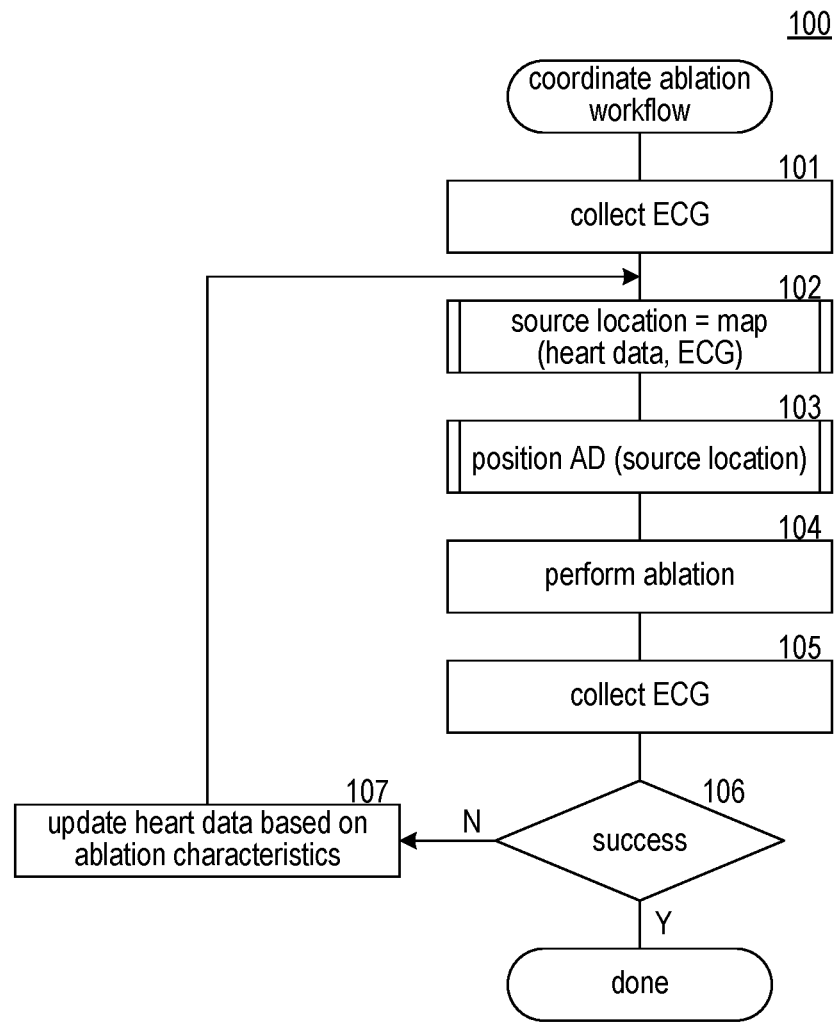
FIG. 1 is a flow diagram that illustrates the processing of a coordinate ablation workflow component of an interactive ablation workflow system in some embodiments.

Methods and systems are provided for treating a patient with an arrhythmia to help ensure that the treatment is successful during an ablation procedure. In some embodiments, an interactive ablation workflow (IAW) system assists an electrophysiologist (EP) during an ablation procedure. The IAW system initially accesses a patient arrhythmia cardiogram collected for a patient during an arrhythmia episode. The IAW system then coordinates the identification of a target location based on the patient arrhythmia cardiogram, the performance of an ablation based on the target location, the collection of a post-ablation patient cardiogram, and the determination of whether the post-ablation cardiogram indicates the ablation was successful. If it was not successful, the process can be repeated starting with the post-ablation patient arrhythmia cardiogram until an ablation is determined to be successful. The IAW system may identify a target location based on a patient arrhythmia cardiogram using one or more mapping techniques described in U.S. Pub. No. 2021/0065906, entitled "Calibration of Simulated Cardiograms" and published on Mar. 4, 2021 ('906 application), which is hereby incorporated by reference. One mapping technique compares a patient arrhythmia cardiogram to a library of library cardiograms that are each associated with a source location. The source location associated with the library cardiogram that is similar to the patient arrhythmia cardiogram may represent the source location of the patient's arrhythmia. That source location may be the target location of an ablation. The library cardiograms may be generated based on simulated electrical activations of hearts with different heart characteristics (or heart data) such as different geometries, electrical properties, scar locations, source locations, ablation locations, and so on. Another mapping technique identifies the source location of an arrhythmia by inputting an arrhythmia cardiogram to a machine learning model that outputs a corresponding source location. The machine learning model may be trained using the library cardiograms labeled with their associated source locations. In addition, the library cardiograms may be calibrated to characteristics of the patient's heart by identifying a subset of the library cardiograms that have similar characteristics (e.g., heart shape and orientation) and selecting a source location based on that subset or training a machine learning model based on that subset.

In some embodiments, the IAW system coordinates an ablation procedure on a patient as follows. The IAW system collects a patient arrhythmia cardiogram during an arrhythmia episode or receives a previously collected patient arrhythmia cardiogram collected during an arrhythmia episode. The arrhythmia episode may be induced using cardiac pacing. The cardiogram may be an electrocardiogram (ECG), a vectorcardiogram (VCG), or another type of cardiogram. The IAW system uses the patient arrhythmia cardiogram to identify a source location of the source of the arrhythmia. For example, the IAW system may submit the patient arrhythmia cardiogram to a mapping system that implements one or more mapping techniques and receives a corresponding source location representing the location of the source of the arrhythmia. The source location may represent the target location for the ablation. In addition, the IAW system may identify an ablation pattern for the ablation using the ablation pattern identification (API) system, as described in the '906 application. Alternatively, the ablation pattern may be provided by a medical provider.

After a source location is identified (and possibly an ablation pattern), the IAW system may coordinate the use of a pacing source to further refine the target location. A pacing source may be inserted into the patient's heart and guided to the source location. The IAW system may employ a guidance technique for guiding the pacing source as described in U.S. application Ser. No. 17/308,400, entitled "Guiding Implantation of an Energy Delivery Component in a Body," and filed on May 25, 2021 ('400 application), which is hereby incorporated by reference. Once the pacing source is located near the source location, the IAW system directs pacing of the pacing source to elicit an arrhythmia and collecting of a cardiogram. If the collected cardiogram does not match the patient arrhythmia cardiogram, the IAW system directs movement of the pacing source to a new location near the last location and again directs pacing and comparing of a collected cardiogram to the patient arrhythmia cardiogram. The IAW system may direct that this processing be repeated until the collected cardiogram matches the patient arrhythmia cardiogram. When they match, the current location of the pacing may be identified as the target location.

In some embodiments, the IAW system displays graphics representing a patient's heart with an indication of one or more source locations superimposed on the heart. A system for generating such a graphic, referred to as a source location (SL) graphic, is described in U.S. Pat. No. 10,709,347, entitled "Heart Graphic Display System," and issued on Jul. 14, 2020 ('347 patent), which is hereby incorporated by reference. The '347 patent describes identifying one or more source locations by identifying library cardiograms that match a patient cardiogram and selecting the source locations that match the library cardiograms. A machine learning model may also be used to identify source locations based on the patient cardiogram. The SL graphic may generate the representation of a heart based on measurements of the geometry of the patient's heart, the geometry of a heart associated with one or more library cardiograms, and/or a standard geometry of a heart. The source locations may be represented by various indicators such as an X marking a source location, color variations such as variations in intensities to distinguish likely source locations from less likely source locations, and so on.

During an electrophysiology procedure, the IAW system may generate and display an SL graphic, referred to as an arrhythmia SL graphic, based on arrhythmia source locations identified based on an arrhythmia cardiogram of the patient. A medical provider may use the arrhythmia SL graphic in planning the medical treatment (e.g., ablation). The IAW system may also generate a pacing SL graphic based on a pacing cardiogram collected during the procedure. The pacing cardiogram may be collected in various ways such as using a 12-lead ECG device, an ablation device that collects ECGs, and so on. The IAW system may interface directly with these devices to receive the pacing cardiogram. The IAW system identifies pacing source locations based on the pacing cardiogram using a library of library cardiograms or a machine learning model, as described above. To generate the pacing SL graphic, the IAW system generates a graphic representing the patient's heart and superimposes the pacing source locations on the graphic as described above. The IAW system may then display both the arrhythmia SL graphic and the pacing SL graphic to assist the medical provider in treating the patient. The IAW system may also display the corresponding arrhythmia cardiogram and pacing cardiogram, which also may displayed without displaying an SL graphic. In some embodiments, the component may add an indication of an arrhythmia source location and a pacing source location to the same heart graphic to generate a combined arrhythmia SL and pacing SL graphic. The arrhythmia source location and the pacing source location may be identified using different graphic representations such as an X and O, different colors, different intensities of a color, and so on.

In some embodiments, the IAW system may generate various similarity metrics to indicate the similarity between an arrhythmia cardiogram and a pacing cardiogram and between arrhythmia source locations and pacing source locations. For example, the IAW system may employ a Pearson correlation technique to generate a similarity metric based on the cardiograms. The IAW system may employ a distance metric to generate a similarity metric based on the source locations. The arrhythmia source locations and the pacing source locations may each be represented as an array of source locations ordered by probability of being the actual source location. The distance metric may be the average of the distances between corresponding source locations of the arrays weighted by the probabilities associated with the source locations. The similarity metrics may be output to a medical provider to assist in treating the patient.

After the target location is identified, the IAW system directs an ablation device to target the target location. The IAW system then activates the ablation device to perform the ablation using the ablation pattern if identified. The IAW system may, for example, output the target location and ablation pattern to an ablation system to control the performing of the ablation or to a medical provider who controls the performing of the ablation.

After the ablation is performed, the IAW system directs attempts to re-elicit the arrhythmia. The attempts may include pacing near the ablation location. If the arrhythmia cannot be re-elicited, the IAW system indicates that the ablation procedure may have been successful. If, however, the arrhythmia is re-elicited, then the IAW system continues the coordination of the ablation procedure. The assessment of whether a cardiogram represents an arrhythmia may be based on an algorithm that inputs a cardiogram and outputs an indication of whether the cardiogram represents an arrhythmia. The algorithm may be a machine learning model trained using cardiograms labeled with whether they represent an arrhythmia. The cardiograms may also be labeled with the type of arrhythmia such as VF, VT, AF, and so on.

To continue the ablation procedure, the IAW system collects ablation characteristics of the ablation and a post-ablation arrhythmia cardiogram. The ablation characteristics may include the actual ablation location, the actual ablation pattern, and the extent of the ablation (e.g., height, width, and depth). The actual ablation location and the actual ablation pattern may be somewhat different from the target location and the ablation pattern determined by the IAW system. The IAW system may automatically collect the ablation characteristics (e.g., from an ablation device) or receive the ablation characteristics from a medical provider.

The IAW system then directs repeating the process of identifying a new source location, generating SL graphics, refining the target location, performing the ablation, and attempting to re-elicit an arrhythmia until an ablation procedure is determined to satisfy a completion criterion, such as failure to re-elicit an arrhythmia, a predefined number of ablations, an indication from the medical provider to terminate the procedure, and so on.

When identifying a new source location, the IAW system may factor in the ablation characteristics of prior ablations. For example, the IAW system may direct creation of a calibrated library of library cardiograms factoring in the ablation characteristics or training a machine learning model using library cardiograms generated from simulations that factor in the ablation characteristics. The IAW system may also run simulations of electrical activations of a heart with configuration information that factors in the ablation characteristics. The electromagnetic output of the simulations may be initialized using the "bootstrapping" technique described in the '906 application. The bootstrapping technique initializes the electromagnetic output to the electromagnetic output of a prior simulation in which an arrhythmia has stabilized. Such bootstrapping may result in the simulation stabilizing the arrhythmia faster than if the electromagnetic output were initialized to zero or random values. When a machine learning model is trained, the model (or classifier) weights of the model may be initialized to weights of a previously trained model. Such initialization may result in training that is faster than if the weights were initialized to zero or random values.

FIG. 1 is a flow diagram that illustrates the processing of a coordinate ablation workflow component of an IAW system in some embodiments. The coordinate ablation workflow component 100 coordinates the overall processing of an ablation procedure. In block 101, the component collects an arrhythmia ECG from the patient during an arrhythmia episode. Alternatively, the arrhythmia ECG may have been previously collected and input to the component. In block 102, the component invokes a map system, passing an indication of heart data of the patient and the arrhythmia ECG, and receives a source location indicating the source of the arrhythmia. The medical provider may need to confirm that the source location should be used as the target location before performing the ablation. In block 103, the component invokes a position ablation device component, passing an indication of the source location to position the ablation device at a target location for the ablation. In block 104, the component directs the performing of the ablation by activating the ablation device. In block 105, the component collects a post-ablation ECG from the patient. In decision block 106, if the post-ablation ECG indicates that the ablation was successful, then the component completes, else the component continues at block 107. In block 107, the component updates the heart data based on ablation characteristics of the ablation and loops to block 102 to perform another ablation.

Figure 2:
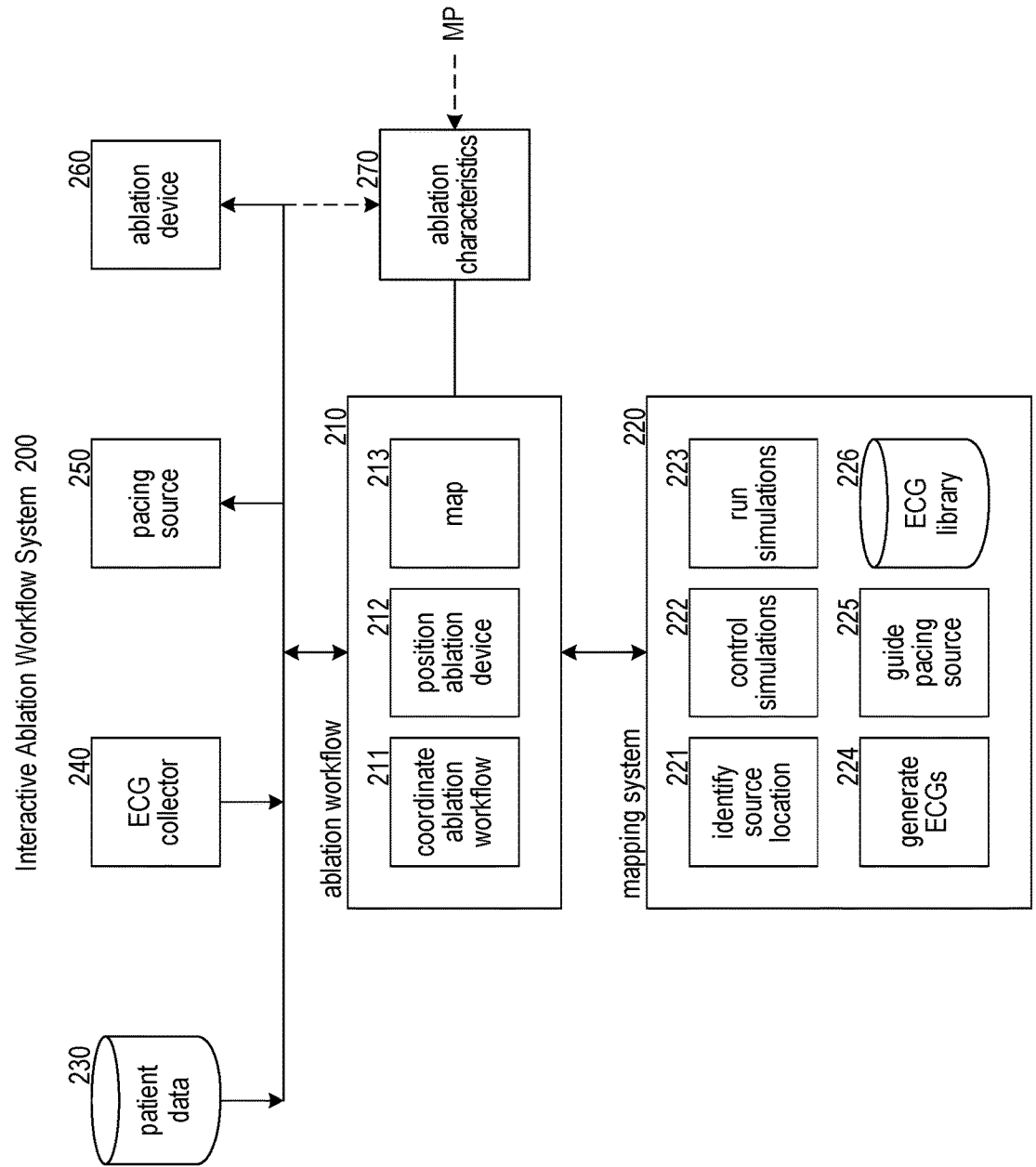
FIG. 2 is a block diagram that illustrates components of an interactive ablation workflow system in some embodiments.

FIG. 2 is a block diagram that illustrates components of an IAW system in some embodiments. The IAW system includes an ablation workflow component 210 that interacts with a mapping system 220 and interfaces with a patient data store 230, an ECG collector 240, a pacing source 250, and an ablation device 260. The ablation workflow component also interfaces with an ablation characteristics component 270. The ablation workflow component includes a coordinate ablation workflow component 211, a position ablation device component 212, and a map component 213. The coordinate ablation workflow component coordinates the overall workflow. The position ablation device component coordinates the positioning of the ablation device at a target location. The map component interacts with the mapping system to identify a source location and an ablation pattern for an ablation. The mapping system includes an identify source location component 221, a control simulations component 222, a run simulations component 223, a generate ECGs component 224, a guide pacing source component 225, and an ECG library 226. The components of the mapping system may implement mapping techniques as described in the '906 application and the '400 application as described above. The components of the mapping system may execute in a cloud computing data center and/or on a local computer. For example, the run simulations component may execute in a cloud data center and the identify source location component may execute on a local computer. The patient data store includes patient heart data of the patient such as heart geometry, orientation, electrical characteristics, scar location, prior ablation characteristics, and so on. The ECG collector collects ECGs from the patient. The pacing source is a device that, when activated, sends out pacing signals. The ablation device, when activated, performs an ablation at the target location to which it is directed and in a specified ablation pattern. The ablation characteristics component collects ablation characteristics from an ablation device or from a medical provider.

The computing systems (e.g., network nodes or collections of network nodes) on which the IAW system and the other described systems may be implemented may include a central processing unit, input devices, output devices (e.g., display devices and speakers), storage devices (e.g., memory and disk drives), network interfaces, graphics processing units, cellular radio link interfaces, global positioning system devices, and so on. The input devices may include keyboards, pointing devices, touch screens, gesture recognition devices (e.g., for air gestures), head and eye tracking devices, microphones for voice recognition, and so on. The computing systems may include high-performance computing systems, cloud-based servers, desktop computers, laptops, tablets, e-readers, personal digital assistants, smartphones, gaming devices, servers, and so on. For example, the simulations and training may be performed using a high-performance computing system, and the classifications may be performed by a tablet. The computing systems may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and other storage. The computer-readable storage media may have recorded on them or may be encoded with computer-executable instructions or logic that implements the IAW system and the other described systems. The data transmission media are used for transmitting data via transitory, propagating signals or carrier waves (e.g., electromagnetism) via a wired or wireless connection. The computing systems may include a secure cryptoprocessor as part of a central processing unit for generating and securely storing keys and for encrypting and decrypting data using the keys.

The IAW system and the other described systems may be described in the general context of computer-executable instructions, such as program modules and components, executed by one or more computers, processors, or other devices. Generally, program modules or components include routines, programs, objects, data structures, and so on that perform tasks or implement data types of the IAW system and the other described systems. Typically, the functionality of the program modules may be combined or distributed as desired in various examples. Aspects of the IAW system and the other described systems may be implemented in hardware using, for example, an application-specific integrated circuit (ASIC) or field programmable gate array (FPGA).

Figure 3:
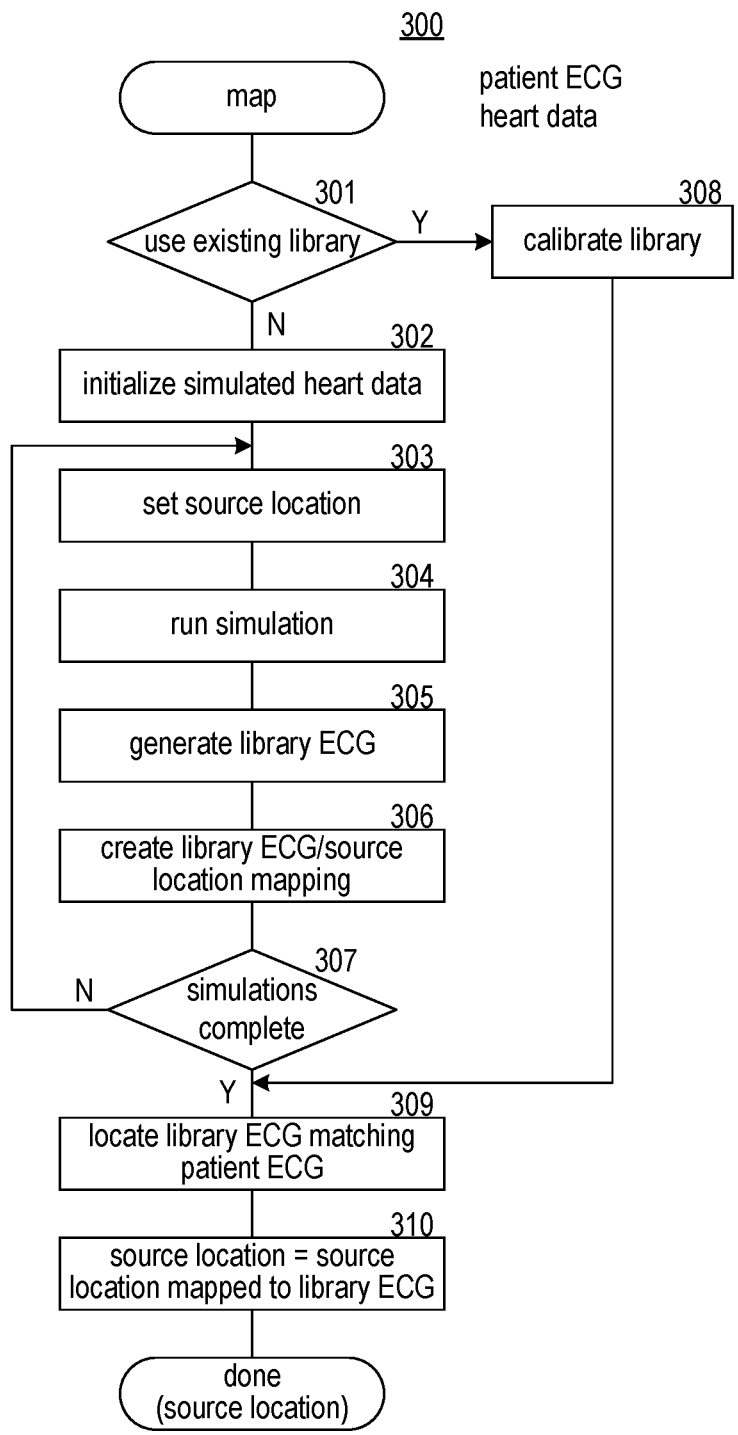
FIG. 3 is a flow diagram that illustrates processing of a map component of the interactive ablation workflow system in some embodiments.

FIG. 3 is a flow diagram that illustrates processing of a map component of the IAW system in some embodiments. The map component 300 is invoked to identify a source location as a possible target location for an ablation. In decision block 301, if an existing library of library ECGs is to be used, then the component continues at block 308, else the component continues at block 302. In block 302, the component initializes simulated heart data based on patient heart data to be used in the simulation. The simulated heart data may be based on the same heart geometry, orientation, electrical characteristics, and so on as the patient heart data. In block 303, the component sets a simulated source location of an arrhythmia for the simulation. In block 304, the component runs a simulation based on the simulated heart data including the simulated source location. In block 305, the component generates a library ECG from the electromagnetic output of the simulation. In block 306, the component creates a mapping of the library ECG to the simulated source location. In decision block 307, if the simulations are complete, then the component continues at block 309, else the component loops to block 303 to set the next simulated source location. In block 308, the component calibrates an existing library to the heart data of the patient, for example, as described in the '906 application. In block 309, the component locates a library ECG that matches the patient ECG. In block 310, the component sets the target source location to the source location to which the library ECG is mapped. The component then completes, indicating the target source location.

Figure 4:
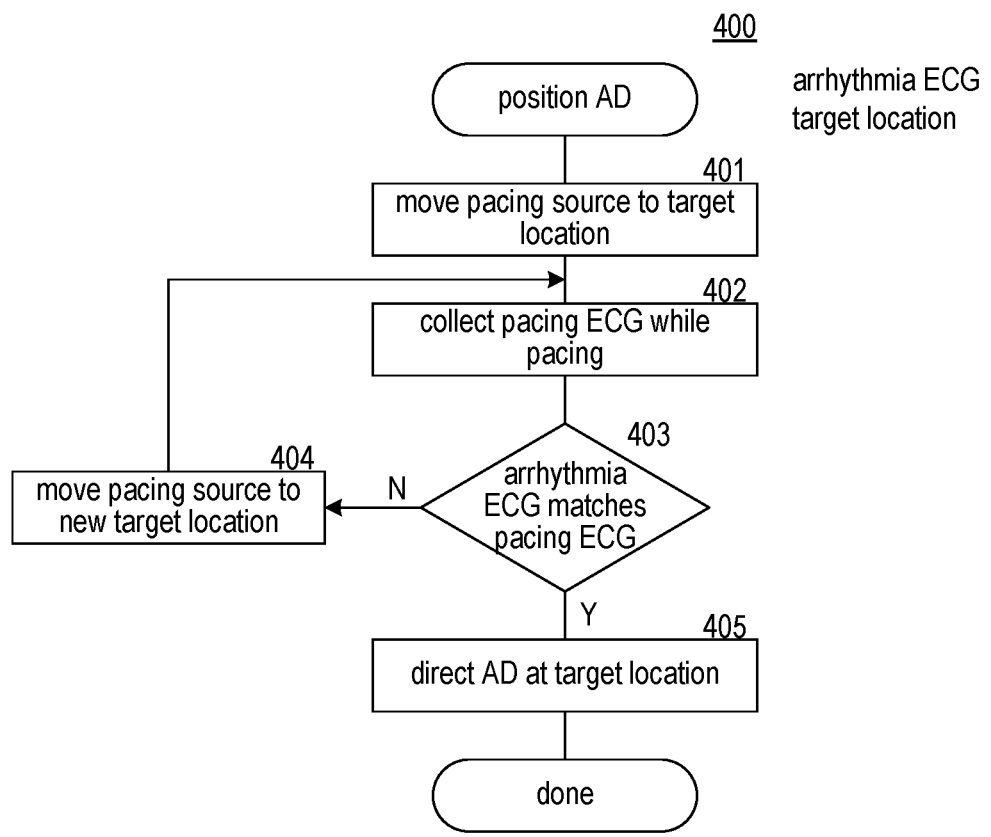
FIG. 4 is a flow diagram that illustrates the processing of a position ablation device component of the interactive ablation workflow system in some embodiments.

FIG. 4 is a flow diagram that illustrates the processing of a position ablation device component of the IAW system in some embodiments. The position ablation device component 400 is passed an indication of an arrhythmia ECG and a target location and directs the ablation device to a refined target location. In block 401, the component directs the moving of the pacing source to the target location. In block 402, the component collects a pacing ECG while pacing the pacing source. In decision block 403, if the arrhythmia ECG matches the pacing ECG, then the component continues at block 405, else the component continues at block 404. In block 404, the component moves the pacing source to a new target location and loops to block 402 to continue the pacing. In block 405, the component directs the ablation device at the target location and then completes.

Figure 5:
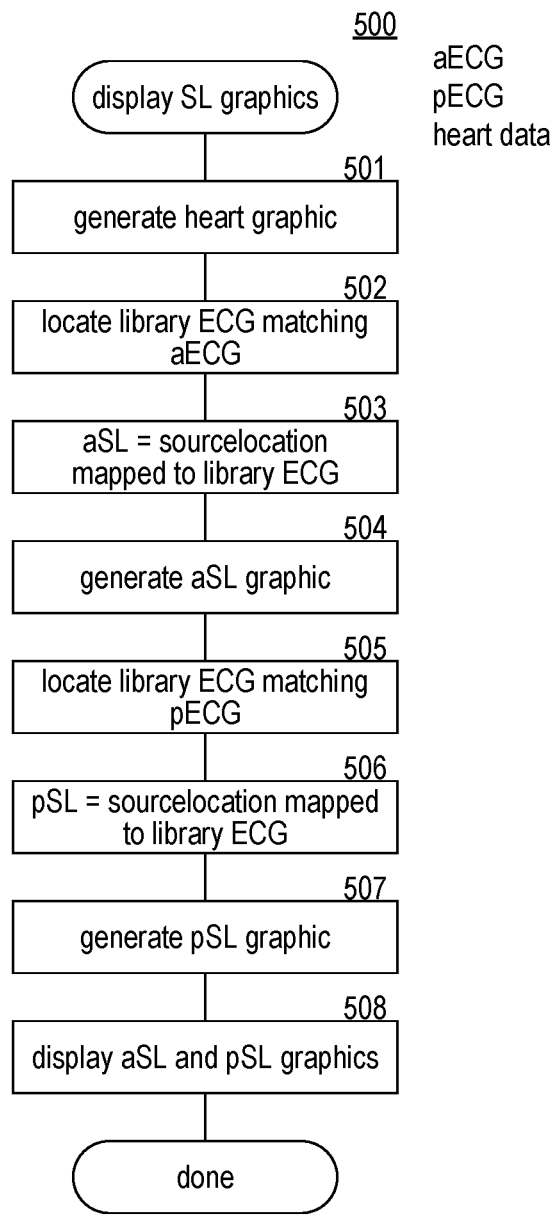
FIG. 5 is a flow diagram that illustrates the processing of a display SL graphics component of the interactive ablation workflow system in some embodiments.

FIG. 5 is a flow diagram that illustrates the processing of a display SL graphics component of the IAW system in some embodiments. The display SL graphics component 500 inputs an arrhythmia ECG (aECG), a pacing ECG (pECG), and heart data of the patient and outputs an arrhythmia source location (aSL) and a pacing source location (pSL) graphic. In block 501, the component generates a heart graphic based on the heart data. In block 502, the component locates a library ECG that matches the aECG. In block 503, the component employs the mapping system to identify an aSL associated with the library ECG. In block 504, the component generates an aSL graphic based on the heart graphic. In block 505, the component locates a library ECG that matches the pECG. In block 506, the component employs the mapping system to identify a pSL associated with the library ECG. In block 507, the component generates a pSL graphic. In block 508, the component displays the aSL and the pSL graphics and completes.

The following paragraphs describe various embodiments of aspects of the IAW system and other systems. An implementation of the systems may employ any combination of the embodiments. The processing described below may be performed by a computing system with a processor that executes computer-executable instructions stored on a computer-readable storage medium that implements the system.

In some embodiments, a method for treating a patient with an arrhythmia is provided. The method collects a first patient arrhythmia cardiogram of the patient. The method identifies a first target location and a first ablation pattern associated with a first library arrhythmia cardiogram that is similar to the first patient arrhythmia cardiogram. The method performs a first ablation near the first target location factoring in the first ablation pattern. The method collects a second patient arrhythmia cardiogram of the patient. The method identifies a second target location and a second ablation pattern associated with a second library arrhythmia cardiogram that is similar to the second patient arrhythmia cardiogram. The second library arrhythmia cardiogram is based on ablation characteristics of the first ablation. The method performs a second ablation near the second target location factoring in the second ablation pattern. In some embodiments, the identification of a target location includes adjusting the target location by repeatedly locating a pacing source based on the target location, collecting a patient pacing cardiogram while pacing, and adjusting the target location based on comparison of the patient pacing cardiogram and a patient arrhythmia cardiogram. In some embodiments, the identification of a target location and an ablation pattern are based on comparison of a patient arrhythmia cardiogram to library arrhythmia cardiograms of a library of library arrhythmia cardiograms. In some embodiments, a library arrhythmia cardiogram is generated based on a simulation of electrical activations based on heart characteristics that includes a source location of an arrhythmia. In some embodiments, the library arrhythmia cardiogram is associated with an ablation pattern based on a simulation of a successful ablation based on heart characteristics that includes the source location and the ablation pattern. In some embodiments, the ablation characteristics of an ablation include location, extent, and ablation pattern. In some embodiments, a second library of second library cardiograms is generated by, for each second library cardiogram, simulating electrical activations factoring in the ablation characteristics and a target location and an ablation pattern. In some embodiments, electromagnetic output of a simulation is initialized based on electromagnetic output of a prior simulation after an arrhythmia has stabilized. In some embodiments, the identification of a target location is based on a machine learning model that is trained using library arrhythmia cardiograms labeled with source locations In some embodiments, the identification of an ablation pattern is based on a machine learning model that is trained using library cardiograms labeled with ablation patterns.

In some embodiments, one or more computing systems are provided for coordinating treatment of a patient with an arrhythmia. The one or more computing systems comprising one or more computer-readable storage mediums that store computer-executable instructions for controlling the one or more computing systems and one or more processors for executing the computer-executable instructions stored in the one or more computer-readable storage mediums. The instructions control the one or more computing systems to access a first patient arrhythmia cardiogram of the patient, identify a first target location associated with a first library arrhythmia cardiogram that is similar to the first patient arrhythmia cardiogram, and output an indication of the first target location. The instructions further control the one or more computing systems to access a second patient arrhythmia cardiogram of the patient collected after a first ablation was performed on the patient based on the first target location, access ablation characteristics of the first ablation, identify a second target location associated with a second library arrhythmia cardiogram that is similar to the second patient arrhythmia cardiogram wherein the second library arrhythmia cardiogram is based on ablation characteristics similar to ablation characteristics of the first ablation, and output an indication of the second target location. In some embodiments, the instructions further control the one or more computing systems to identify a first arrhythmia pattern associated with a first library arrhythmia cardiogram that is similar to the first patient arrhythmia cardiogram and to output an indication of the first ablation pattern. In some embodiments, the indication of a target location is output to a device for controlling an ablation device. In some embodiments, the instructions that identify a target location further control the one or more computing systems to refine the target location by repeatedly directing positioning of a pacing source based on the target location, directing pacing by the pacing source, directing collecting of a patient pacing cardiogram while the pacing source paces, and adjusting the target location based on comparison of the patient pacing cardiogram and a patient arrhythmia cardiogram. In some embodiments, identification of a target location is based on comparison of a patient arrhythmia cardiogram to library arrhythmia cardiograms of a library of library arrhythmia cardiograms. In some embodiments, a library arrhythmia cardiogram is generated based on a simulation of electrical activations of a heart based on heart characteristics that include a source location of an arrhythmia. In some embodiments, the library arrhythmia cardiogram is associated with an ablation pattern based on a simulation of a successful ablation based on the heart characteristics that includes the source location and the ablation pattern. In some embodiments, the ablation characteristics of an ablation include one or more of location, extent, and ablation pattern. In some embodiments, a second library of second library cardiograms is generated by, for each second library cardiogram, simulating electrical activations factoring in the ablation characteristics and a target location. In some embodiments, electromagnetic output of a simulation is initialized based on electromagnetic output of a prior simulation after an arrhythmia of the prior simulation has stabilized. In some embodiments, the identification of a target location is based on a machine learning model that is trained using library arrhythmia cardiograms labeled with source locations. In some embodiments, the instructions further control the one or more computing systems to identify an arrhythmia pattern associated with a library arrhythmia cardiogram that is similar to the patient arrhythmia cardiogram wherein the identification of the ablation pattern is based on a machine learning model that is trained using library cardiograms labeled with ablation patterns.

In some embodiments, one or more computer-readable storage media storing computer-executable instructions for controlling one or more computing systems to coordinate treatment of a patient with an arrhythmia are provided. The instructions identify a first target location and a first ablation pattern associated with a first library arrhythmia cardiogram that is similar to a first patient arrhythmia cardiogram. The instructions control directing an ablation device at the first target location. The instructions control activation of the ablation device to perform a first ablation at the first target location and based on the first ablation pattern. The instructions control identifying a second target location and a second ablation pattern associated with a second library arrhythmia cardiogram that is similar to a second patient arrhythmia cardiogram collected after the first ablation. The second library arrhythmia cardiogram is based on ablation characteristics of the first ablation. The instructions control directing the ablation device at the second target location. The instructions direct activation the ablation device to perform a second ablation at the second target location and based on the second ablation pattern. In some embodiments, the instructions further control collection of the first patient arrhythmia cardiogram and the second patient arrhythmia cardiogram. In some embodiments, the ablation characteristics are collected from the ablation device. In some embodiments, the ablation characteristics are received from a person.

In some embodiments, a method performed by one or more computing devices to control an ablation procedure performed a patient. The method accesses a patient cardiogram of the patient. The method repeats the following until a termination criterion is satisfied. The method identifies a target location and an ablation pattern associated with a library cardiogram that is similar to the patient cardiogram. The library cardiogram is associated with ablation characteristics similar to ablation characteristics of a prior ablation procedure, if any, performed on a patient. The method controls directing the ablation device at the target location. The method controls activation of the ablation device to perform an ablation at the target location and based on the ablation pattern. The method accesses a patient cardiogram of the patient that is collected after the ablation. In some embodiments, the termination criterion is satisfied based on the patient cardiogram indicating no arrhythmia. In some embodiments, a library cardiogram is associated with heart characteristics that are is similar to heart characteristics of the patient. In some embodiments, the heart characteristics include heart geometry and electrical characteristics of the heart. In some embodiments, the library cardiogram is a cardiogram of a cardiogram library that includes cardiograms collected from people. In some embodiments, the library cardiogram is a cardiogram of a cardiogram that includes cardiograms generated based on simulations of electrical activation of a heart based on heart characteristics. In some embodiments, the controlling of the directing of the ablation device further includes locating a pacing source based on the target location, collecting a patient pacing cardiogram while the pacing source paces, and adjusting the target location based on comparison of the patient pacing cardiogram and the patient cardiogram.

In some embodiments, a method performed by one or more computing devices is provided for displaying graphics relating to a source location of an arrhythmia. The method accesses an arrhythmia cardiogram and a pacing cardiogram collected from a patient. The pacing cardiogram is collected during a client procedure. The method generates a heart graphic to represent the heart of the patient. The method identifies an arrhythmia source location associated with the arrhythmia cardiogram. The method generates an arrhythmia source location graphic by adding an indication of the arrhythmia source location to a graphic derived from the generated heart graphic. The method identifies a pacing source location associated with the pacing cardiogram. The method generates a pacing source location graphic by adding an indication of the pacing location to a graphic derived from the generated heart graphic. The method displays the arrhythmia source location graphic and the pacing source location graphic. In some embodiments, the arrhythmia source location graphic and the pacing source location graphic are represented by the generated heart graphic with the indication of the arrhythmia location and the indication of the pacing location added to the same generated heart graphic. In some embodiments, the method displays an arrhythmia cardiogram and a pacing cardiogram simultaneously with the arrhythmia source location graphic and the pacing source location graphic. In some embodiments, the arrhythmia source location and the pacing source location are identified based on a library of library cardiograms. In some embodiments, the library cardiograms include simulated cardiograms. In some embodiments, the library cardiograms include patient cardiograms. In some embodiments, the pacing source location is identified during a clinical procedure for the patient. In some embodiments, the identifying of a pacing source location and the generating of a pacing source location graphic are performed for different pacing locations during a clinical procedure. In some embodiments, multiple arrhythmia source locations are identified based on an arrhythmia cardiogram and multiple pacing source locations are identified based on a pacing cardiogram and further comprising generating a metric indicating similarity between the arrhythmia source locations and the pacing source locations and displaying an indication of the metric.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims.

We claim:

1. A method performed by one or more computing systems for treating a patient with an arrhythmia during an ablation procedure, the method comprising:
   accessing a patient cardiogram that is an arrhythmia cardiogram; and
   for each of a plurality of ablations performed during the ablation procedure,
      identifying a target location and an ablation pattern based on a library cardiogram that is similar to the patient cardiogram factoring in one or more ablation characteristics of an ablation if any ablation is performed during the ablation procedure;
      displaying a graphic of a heart with an indication of the target location;
      for each of a plurality of guidance pacing locations within the heart of the patient as an ablation device is moved to the target location,
         receiving a guidance pacing cardiogram collected while the ablation device paces at that guidance pacing location;
         identifying that guidance pacing location based on a library cardiogram that is similar to the guidance pacing cardiogram, the library cardiogram associated with a location; and
         displaying on the graphic an indication of that guidance pacing location;
      for each of a plurality of eliciting pacing locations,
         receiving an elicited pacing cardiogram collected while the ablation device is pacing at that eliciting pacing location; and
         determining whether the elicited pacing cardiogram is similar to the patient cardiogram;
      outputting an indication that an ablation is to be performed factoring in the ablation pattern;
      accessing another patient cardiogram after the ablation is performed, the other patient cardiogram being an arrhythmia cardiogram; and
      based the determination that the other patient cardiogram is an arrhythmia,
         accessing actual characteristics of the last ablation that was performed including an actual ablation pattern and an actual ablation location of the last ablation; and
         running simulations of electrical activity of a heart, at least some of the simulations based on the actual characteristics and a simulated source location to generate a library cardiogram for each simulation
   wherein similarity is based on a similarity metric.

2. The method of claim 1 wherein electrical activity of a simulation is initialized based on simulated electrical activity of a prior simulation after an arrhythmia has stabilized.

3. The method of claim 1 wherein the identification of the target location is based on a machine learning model that is trained using training library cardiograms labeled with source locations.

4. The method of claim 1 wherein the identification of the ablation pattern is based on a machine learning model that is trained using training library cardiograms labeled with ablation patterns.

5. The method of claim 1 further comprising determining whether the other patient cardiogram is an arrhythmia cardiogram based on a machine learning model trained with training data that includes training cardiograms labeled with indications of whether the training cardiograms are arrhythmia cardiograms.

6. One or more computing systems for coordinating treatment of a patient with an arrhythmia during an ablation procedure, the one or more computing systems comprising:
   one or more computer-readable storage mediums storing computer-executable instructions for controlling the one or more computing systems to:
      access a first patient arrhythmia cardiogram of the patient;
      identify a first target location based on similarity of one or more first library arrhythmia cardiograms of a library of library cardiograms to the first patient arrhythmia cardiogram;
      display an indication of the first target location on a graphic of a heart;
      display on the graphic guidance locations as an ablation device is moved to the first target location, each guidance location identified based on pacing at that guidance location, collecting a guidance cardiogram while pacing, and identifying the guidance location based on similarity between the guidance cardiogram and library cardiograms of a guidance library of library guidance cardiograms;
      direct eliciting of the arrhythmia when the ablation device has been moved to the first target location;

direct performing of a first ablation when the arrhythmia is elicited;

after the first ablation is performed, access a second patient arrhythmia cardiogram of the patient collected after the first ablation was performed on the patient based on the first target location;

access actual ablation characteristics of the first ablation that include an actual ablation pattern and an actual ablation location;

run simulations of electrical activity of a heart, at least some of the simulations based on the actual ablation characteristics and a simulated source location to generate a simulated arrhythmia cardiogram for at least some of the simulations;

identify a second target location based on similarity of simulated arrhythmia cardiograms to the second patient arrhythmia cardiogram, the simulated arrhythmia cardiograms associated with source locations;

display on the graphic an indication of the second target location;

direct eliciting of the arrhythmia; and direct performing of a second ablation when the arrhythmia is elicited; and one or more processors for executing one or more of the computer-executable instructions stored in the one or more computer-readable storage mediums.

7. The one or more computing systems of claim 6 wherein the instructions further control the one or more computing systems to identify a first ablation pattern associated with one or more first library arrhythmia cardiograms and to output an indication of the first ablation pattern.

8. The one or more computing systems of claim 6 wherein an indication of the first target location is output to a device for controlling an ablation device.

9. The one or more computing systems of claim 6 wherein a library cardiogram of the library is associated with an ablation pattern based on a simulation of a successful ablation based on heart characteristics that include a simulated source location and the ablation pattern.

10. The one or more computing systems of claim 6 wherein electromagnetic output of a simulation is initialized based on electromagnetic output of a prior simulation after an arrhythmia of the prior simulation has stabilized.

11. The one or more computing systems of claim 6 wherein the identification of at least one of the first target location and the second target location is based on a machine learning model that is trained using library cardiograms labeled with source locations.

12. The one or more computing systems of claim 6 wherein the instructions further control the one or more computing systems to identify an ablation pattern associated with the first library arrhythmia cardiogram and wherein the identification of the ablation pattern is based on a machine learning model that is trained using library cardiograms labeled with ablation patterns.

13. One or more computer-readable storage media storing computer-executable instructions for controlling one or more computing systems to coordinate treatment of a patient with an arrhythmia, the instructions including instructions to, during an ablation procedure:

identify a first target location and a first ablation pattern based on similarity of a first library arrhythmia cardiogram to a first patient arrhythmia cardiogram;

direct an ablation device to the first target location;

direct eliciting of the arrhythmia;

after the arrhythmia is elicited, direct activation of the ablation device to perform a first ablation based on the first ablation pattern;

after the first ablation is performed, direct eliciting of the arrhythmia and collecting of a second patient arrhythmia cardiogram and accessing actual ablation characteristics of the first ablation including an actual ablation pattern and an actual ablation location;

identify a second ablation pattern and a second target location based on similarity of one or more simulated cardiograms that are each associated with a source location to a second patient arrhythmia cardiogram, the one or more simulated cardiograms generated by simulating electrical activations of a heart with a simulated source location and with a prior ablation pattern and a prior ablation location, wherein the similarity factoring in similarity of a prior ablation pattern and a prior ablation location to the actual ablation pattern and the actual ablation location;

output an indication that the ablation device is to be activated to perform a second ablation based on the second ablation pattern and the second target location; and after the second ablation is performed, direct attempting to elicit the arrhythmia to assist in determining whether to terminate the ablation procedure based on the arrhythmia not being elicited.

14. The one or more computer-readable storage media of claim 13 wherein the instructions further control collection of the first patient arrhythmia cardiogram and the second patient arrhythmia cardiogram.

15. The one or more computer-readable storage media of claim 13 wherein the actual ablation characteristics are collected from the ablation device.

16. The one or more computer-readable storage media of claim 13 wherein the actual ablation characteristics are received from a person.

17. A method performed by one or more computing devices to control an ablation procedure performed on a patient with an arrhythmia, the method comprising:

repeating for each of a plurality of patient cardiograms until a termination criterion is satisfied:

identifying a simulated cardiogram based on comparison of the simulated cardiogram to that patient cardiogram;

identifying a target location and an ablation pattern based on the simulated cardiogram;

directing guiding an ablation device to the target location;

directing first eliciting of the arrhythmia based on pacing at pacing locations after the ablation device is guided to the target location wherein the arrhythmia is determined to be elicited based on comparison of the patient cardiogram to a cardiogram collected during the first eliciting;

after the arrhythmia is elicited, directing activation of the ablation device to perform an ablation based on the ablation pattern; and after the ablation is performed, directing second eliciting of the arrhythmia wherein the arrhythmia is determined to be elicited based on comparison of the patient cardiogram to a new patient cardiogram collected during the second eliciting and when the termination criterion is not satisfied, accessing actual ablation characteristics of the ablation including an actual ablation pattern and an actual ablation location; and running simulations of electrical activity of a heart based on the actual ablation characteristics and a simulated source location wherein the termination criterion is based on the arrhythmia not being elicited.

18. The method of claim 17 wherein the identified simulated cardiogram is associated with heart characteristics that are similar to heart characteristics of the patient.

19. The method of claim 18 wherein the heart characteristics include heart geometry and electrical characteristics of the heart.

20. One or more computing systems to support an ablation procedure performed on a patient with an arrhythmia, the one or more computing systems comprising:

one or more computer-readable storage mediums that store computer-executable instructions for controlling the one or more computing systems to for each of a plurality of patient cardiograms that are arrhythmia cardiograms:

identify a target ablation location and an ablation pattern based on the patient cardiogram and based on simulated cardiograms, simulated source locations, and simulated ablation patterns;

output guidance locations to guide an ablation device to the target ablation location, the guidance locations identified based on guidance cardiograms that are collected while pacing at guidance locations and based on simulated cardiograms that are each associated with a location within a heart;

output an indication to elicit the arrhythmia based on pacing at eliciting locations after the ablation device is guided to the target ablation location;

after the arrhythmia is elicited at an eliciting location, output an indication of the ablation pattern and that eliciting location to support performing an ablation at that eliciting location based on the ablation pattern; and after the ablation is performed, output an indication to attempt to elicit another arrhythmia;

access another patient cardiogram collected when attempting to elicit another arrhythmia; and when another arrhythmia is elicited, access actual ablation characteristics of the ablation including an actual ablation pattern and an actual ablation location;

identify another target ablation location and another ablation pattern based on the other patient cardiogram, the actual ablation pattern, and the actual ablation location and based on simulated cardiograms, simulated source locations, prior ablation patterns, and prior ablation locations used in simulations of electrical activity of a heart; and output an indication of the other ablation pattern and the other target ablation location to support performing of another ablation; and one or more processors for controlling the one or more computing systems to execute one or more of the computer-executable instructions.

* * * * *